US012703690B2

(12) United States Patent
Lishchynskyi et al.

(10) Patent No.: US 12,703,690 B2
(45) Date of Patent: Aug. 11, 2026

(54) PROCESS FOR PREPARING ALKYL-4-OXOTETRAHYDROFURAN-2-CARBOXYLATE

(71) Applicant: Bayer Aktiengesellschaft, Leverkusen (DE)

(72) Inventors: Anton Lishchynskyi, Leverkusen (DE); Carlos Moriana Herraiz, Leverkusen (DE); Günter Hömberger, Leverkusen (DE); Mark James Ford, Leverkusen (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 411 days.

(21) Appl. No.: 18/279,626

(22) PCT Filed: Feb. 28, 2022

(86) PCT No.: PCT/EP2022/054925
§ 371 (c)(1),
(2) Date: Aug. 31, 2023

(87) PCT Pub. No.: WO2022/184612
PCT Pub. Date: Sep. 9, 2022

(65) Prior Publication Data

US 2024/0158362 A1 May 16, 2024

(30) Foreign Application Priority Data

Mar. 3, 2021 (EP) .................................... 21160527

(51) Int. Cl.
*C07D 307/32* (2006.01)

(52) U.S. Cl.
CPC .................................. *C07D 307/32* (2013.01)

(58) Field of Classification Search
CPC .................................................... C07D 307/32
USPC ......................................................... 549/475
See application file for complete search history.

(56) References Cited

U.S. PATENT DOCUMENTS 9,078,442 B2 7/2015 Willms
9,516,880 B2 12/2016 Haaf et al.
11,597,724 B2 3/2023 Peters et al.
11,613,522 B2 3/2023 Peters et al.
12,171,230 B2 12/2024 Trabold et al.
12,185,723 B2 1/2025 Van Almsick
12,319,664 B2 6/2025 Bojack et al.
2022/0053762 A1 2/2022 Trabold
2022/0386605 A1 12/2022 Lorentz et al.
2023/0104990 A1 4/2023 Olenik
2023/0189808 A1 6/2023 Dittgen et al.
2023/0200390 A1 6/2023 Dittgen et al.
2023/0200393 A1 6/2023 Dittgen et al.
2023/0200394 A1 6/2023 Dittgen et al.
2023/0217926 A1 7/2023 Dittgen et al.
2023/0240297 A1 8/2023 Dittgen et al.
2023/0265062 A1 8/2023 Hoemberger et al.
2023/0276792 A1 9/2023 Dittgen et al.
2023/0339876 A1 10/2023 Pazenok et al.
2023/0348366 A1 11/2023 Rembiak
2024/0010626 A1 1/2024 Pazenok
2024/0132443 A1 4/2024 Lishchynskyi et al.
2024/0166616 A1 5/2024 Lishchynskyi et al.
2025/0042863 A1 2/2025 Cibu et al.
2025/0057164 A1 2/2025 Lorentz et al.
2025/0122158 A1 4/2025 Lishchynskyi et al.

FOREIGN PATENT DOCUMENTS

WO 2014048940 A2 4/2014
WO 2018228985 A1 12/2018
WO 2019034602 A1 2/2019
WO 2022069554 A1 4/2022
WO 2022251154 A1 12/2022
WO 2023001679 A1 1/2023
WO 2023274870 A1 1/2023

OTHER PUBLICATIONS

International Preliminary Report on Patentability from PCT Application No. PCT/EP2022/054925, mailed Aug. 29, 2023.
Okada, et al., "Synthesis and Properties of New Polyesters Having Tetrahydrofuran Rings in Their Main Chains", Journal of Polymer Science Part A: Polymer Chemistry Edition, 1993, pp. 1135-1140, vol. 31, No. 5.
Zwicky, et al., "Synthesis and pharmacological propertiesof desmethylmuscarone and the stereoisomeric desmethylmuscarines The base strengths of the isomeric normuscarines", Helvetica Chimica Acta, 1959, pp. 1177-1189, No. 123.

*Primary Examiner* — Charanjit Aulakh
(74) *Attorney, Agent, or Firm* — Paul D. Tietz; Michael Vanengelen

(57) ABSTRACT

The present invention relates to a novel method for preparing alkyl 4-oxotetrahydrofuran-2-carboxylate (I)

(I)

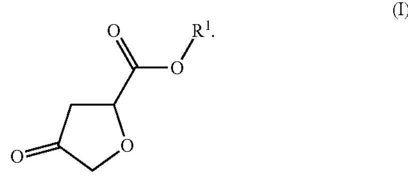

20 Claims, No Drawings

PROCESS FOR PREPARING ALKYL-4-OXOTETRAHYDROFURAN-2-CARBOXYLATE

The present application is a 35 U.S.C. § 371 national phase entry of International Application No. PCT/EP2022/054925, filed on Feb. 28, 2022, which claims priority to European Patent Application No. 21160527.4, filed Mar. 3, 2021, the contents of each of which are hereby incorporated by reference in their entirety.

The present invention relates to a novel method for preparing alkyl 4-oxotetrahydrofuran-2-carboxylate (I).

Methyl 4-oxotetrahydrofuran-2-carboxylate of formula (I) is an important precursor of agrochemical (cf. WO2018/228985) active substances.

The synthesis of methyl 4-oxotetrahydrofuran-2-carboxylate of formula (I) is known, e.g. from Helv. Chim. Acta 1959, 1177 and WO 2016/205633. However, if starting from dimethyl (Z)-butenedioate, three reaction steps are necessary to prepare methyl 4-oxotetrahydrofuran-2-carboxylate of formula (I), which is accompanied by a loss of yield. Moreover, the reagents that are used in the prior art (for example sodium powder, NaH, $TMSCHN_2$, $CH_2N_2$) are unsuitable for an industrial-scale synthesis, since safe handling of these chemicals on a large scale is difficult or they are highly toxic.

In the light of the prior art described above, the object of the present invention is to develop, starting from compounds of general formula (II) and (III) in only two reaction steps, a method for preparing compounds of general formula (I) that is also suitable for production on a large scale.

The object described above is achieved by a method for preparing compounds of general formula (I)

(I)

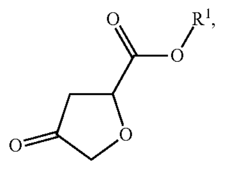

in which $R^1$ is $(C_1-C_4)$ alkyl, characterized in that compounds of general formula (II)

(II)

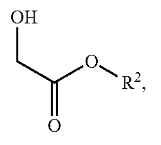

in which $R^2$ is $(C_1-C_4)$ alkyl, afford with compounds of general formula (III)

(III)

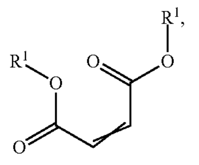

in which $R^1$ is as defined above, through addition of MO—Z in Z—OH, in which

M is an alkali metal ion and

Z is $(C_1-C_4)$ alkyl, t-butyl excepted, cyclization products of general formula (IV)

(IV)

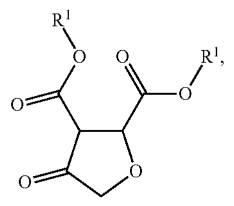

in which $R^1$ is as defined above, which under non-hydrolytic conditions undergo dealkoxycarbonylation and react to form compounds of general formula (I).

Preferred definitions of the radicals for the compounds of general formulas (I), (II), (III), (IV), MO—Z and Z—OH are as follows:

$R^1$ is ethyl or methyl, $R^2$ is ethyl or methyl,

M is sodium or potassium,

Z is ethyl or methyl.

Particularly preferred definitions of the radicals for the compounds of general formulas (I), (II), (III), (IV), MO—Z and Z—OH are as follows:

$R^1$ is methyl, $R^2$ is methyl,

M is sodium,

Z is methyl.

Elucidation of the Method

The reaction conditions for preparing compounds of general formula (I) are elucidated in detail hereinbelow.

Scheme 1

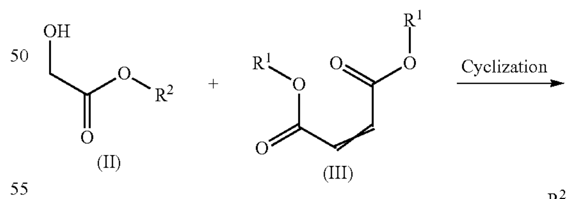

(II) + (III)

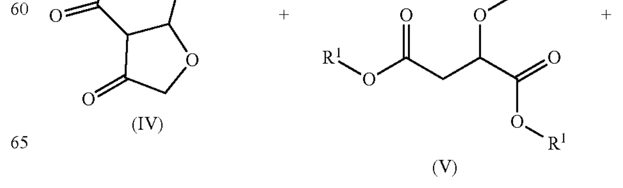

(IV) + (V) +

-continued

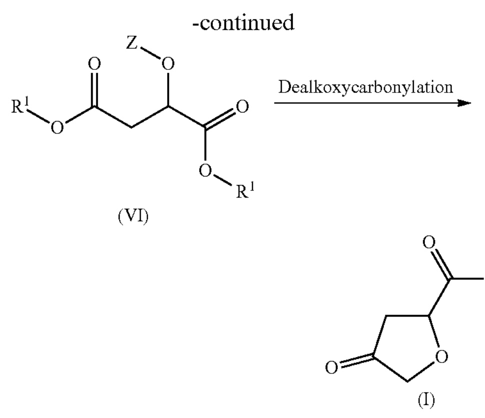

(VI)

(I)

The compounds of general formula (II) react with compounds of general formula (III) in the presence of MO—Z in Z—OH to form cyclization products of general formula (IV), which under non-hydrolytic conditions undergo dealkoxycarbonylation and react to form compounds of general formula (I).

During the cyclization, in addition to the actual product there may also be present in the reaction mixture compounds of general formula (IV) and also residual intermediates of general formulas (V) and (VI), which under the given reaction conditions react further to form the product of general formula (IV).

The compounds of general formula (II) and (III) are commercially available. The compounds of general formula (III) can surprisingly be used in the form of the E isomer or the Z isomer and lead to a comparable result. This is not known from the literature. Under the reaction conditions, an isomerization between the E isomer and the Z isomer takes place.

The compounds of general formula (I) have a stereocentre. The product is consequently present in the form of a racemate.

Cyclization:

The cyclization is known from the prior art, where it is carried out using NaH or sodium powder (Helv. Chim. Acta 1959, 1177; WO 2016/205633). These reagents are unsuitable for an industrial-scale synthesis, since their safe handling on a large scale is difficult.

The yield of the reaction according to the invention is higher (>30%) than that of the reaction using NaH or sodium powder described in the prior art (<30%). Moreover, the use of the alkoxide base means that the reaction can be employed on an industrial scale too.

Advantageous for achieving a high yield is the slow addition of the alkoxide base, for example through metered addition.

In addition, the equilibrium of the reaction to form the product can be shifted when the alcohol used as solvent and additionally formed during the cyclization is removed by distillation. The yield increases.

The molar ratio of MO—Z to compounds of general formula (II) is 0.8 to 3 equivalents, preferably 0.9 to 1.2 equivalents.

The molar ratio of Z—OH to compounds of general formula (II) is 1 to 10 equivalents, preferably 4 to 7 equivalents.

The molar ratio of compounds of general formula (II) to compounds of general formula (III) is 0.8 to 3 equivalents, preferably 0.9 to 1.2 equivalents.

The temperature may be varied within a wide range and depends for example on the solvent. It is for the reaction preferably 15 to 70° C., particularly preferably 40 to 60° C.

The reaction is normally carried out in a solvent, preferably in anisole, THF, toluene, xylene or Me-THF.

The solvent may contain Z—OH. Preferably, this is an anhydrous ("dry" or absolute) solvent.

Dealkoxycarbonylation (Organic Reactions, Vol. 81):

Whereas with sulfuric acid in water (see Helv. Chim. Acta 1959, 1177; WO 2016/205633), ester cleavage/decarboxylation to 4-oxotetrahydrofuran-2-carboxylic acid takes place, under non-hydrolytic, e.g. anhydrous, reaction conditions, the ester in compounds of general formula (I) remains present, which means there is no need for the additional step of renewed esterification, which in the prior art is carried out with $CH_2N_2$. There is consequently also no need for the numerous extractions necessary in the prior art of the 4-oxotetrahydrofuran-2-carboxylic acid, which is difficult to isolate from water.

The yield can consequently be increased substantially (>95% versus 75% with sulfuric acid in the prior art). Toxic reagents such as diazomethane can be dispensed with.

The reagent (see Table 1) is used in excess optionally in combination with a solvent. Preferably, the reagent is also used as the solvent.

The temperature for the reaction depends on the reagent/solvent.

Table 1 lists some of these reaction conditions by way of example, but without any limitation thereto.

TABLE 1

| Dealkoxycarbonylation | | |
|---|---|---|
| Conditions (Reagent = solvent) | Temp./° C. | Time/hours |
| Acetic acid | 118 | 6 |
| Acetic acid/trifluoroacetic acid | 115-118 | 25 |
| Propionic acid | 140 | 18 |
| $B(OH)_3$ | 145-175 | 4 |

EXAMPLES

The present invention is elucidated in more detail by the examples that follow, without restriction of the invention thereto.

Measurement Methods

The products were characterized by $^1H$ NMR.

Example 1

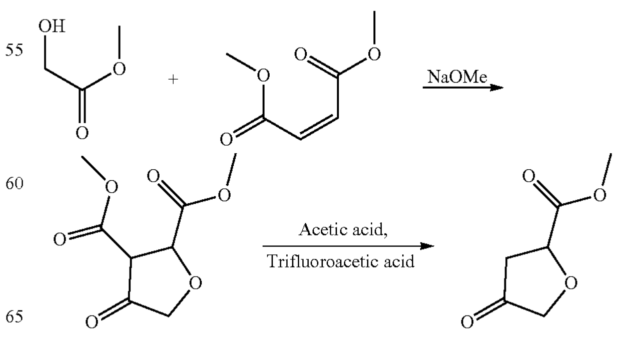

Methyl 4-oxotetrahydrofuran-2,3-dicarboxylate 356 g of methyl glycolate (3.95 mol) and 541 g of dimethyl maleate (3.75 mol) are added together with 2.175 l of anisole to a vessel equipped with a heating/cooling jacket (6 l). The mixture is heated to 49° C. and then 783 g of 30% sodium methoxide (NaOMe=NaOMethyl) in methanol is added over 6 hours. During the first minutes, the internal temperature rises to 55° C. and then remains at 50° C. After approx. 30% of the base has been added, the reaction mixture becomes turbid and a solid precipitates. At the end of the addition of the base, a brownish suspension that is still easily stirrable is present. The reaction mixture is cooled to 20° C. and stirred overnight. The next day, the reaction mixture is heated to 50° C. (55° C. heating jacket) and 849 g of methanol is over a period of 6 hours removed by distillation at a pressure of 360 mbar (at the beginning) to 60 mbar (at the end). The reaction mixture is then cooled to 20° C. and stirred overnight. This reaction mixture is then added to a mixture of dilute sulfuric acid prepared from 2.373 l of water and 225 g of concentrated sulfuric acid (2.17 mol) contained in a vessel equipped with a heating/cooling jacket (6 l), at 10° C. The reaction mixture is stirred for 2 hours at 10 to 12° C., then warmed to 20° C. The two-phase mixture is then separated and the aqueous phase is extracted with anisole. The combined organic phases are concentrated to 990 g.

Methyl 4-oxotetrahydrofuran-2-carboxylate

The oil from the previous reaction step is added to 1200 ml of acetic acid. To this is added 67.6 g of trifluoroacetic acid and the reaction mixture is stirred at 115 to 118° C. for 24 hours. The acetic acid is then distilled off and the product is purified by distillation. The product is an oil (350 g, 66% yield).

NMR Data $^{1}$H-NMR (600 MHz, DMSO-d6): δ (ppm)=4.97 (dd, J=8.8, 5.1 Hz, 1H), 4.02 (d, J=16.7 Hz, 1H), 3.99 (d, J=16.7 Hz, 1H), 3.69 (s, 3H), 2.88 (dd, J=18.2, 8.8 Hz, 1H), 2.60 (dd, J=18.2, 5.1 Hz, 1H).

TABLE 2

Comparison of the yield

| | Reaction conditions | Overall yield |
|---|---|---|
| Example No. 1 | NaOMe/acetic acid/trifluoroacetic acid | 66% |
| Comparative example: Helv. Chim. Acta 1959, 1177 | Sodium powder, sulfuric acid, water, $CH_2N_2$ | 23% |

The invention claimed is:

1. A method for preparing a compound of general formula (I)

(I)

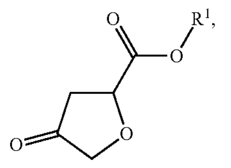

in which $R^1$ is ($C_1$-$C_4$) alkyl, the method comprising:

reacting a compound of general formula (II)

(II)

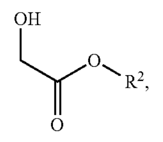

in which $R^2$ is ($C_1$-$C_4$) alkyl, with a compound of general formula (III)

(III)

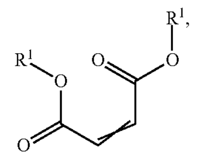

in which $R^1$ is as defined above, in the presence of MO—Z in an alcohol Z—OH, in which M is an alkali metal ion and Z is ($C_1$-$C_4$) alkyl, not including t-butyl;

forming, in a cyclization reaction, a cyclization product of general formula (IV)

(IV)

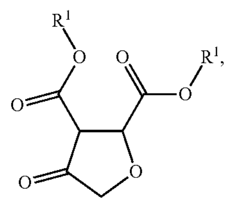

in which $R^1$ is as defined for formula (I); and reacting, under non-hydrolytic conditions, the cyclization products in a dealkoxycarbonylation reaction to form the compound of general formula (I).

2. The method according to claim 1, wherein:

$R^1$ is ethyl or methyl, $R^2$ is ethyl or methyl,

M is sodium or potassium, and

Z is ethyl or methyl.

3. The method according to claim 2, wherein:

$R^1$ is methyl, $R^2$ is methyl,

M is sodium, and

Z is methyl.

4. The method according to claim 1, wherein, in addition to the cyclization product having the general formula (IV), intermediates (V) and (VI) also form (V)

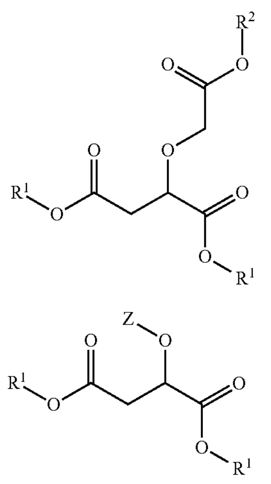

(VI)

in which $R^1$ is as defined for formula (I) and $R^2$ is as defined for formula (II), wherein the intermediates (V) and (VI) react further to form the compound of formula (IV).

5. The method according to claim 1, wherein the alcohol Z—OH is removed by distillation during the cyclization reaction.

6. The method according to claim 1, wherein the cyclization is carried out at a temperature of from 15 to 70° C.

7. The method according to claim 6, wherein the cyclization reaction is carried out at a temperature of from 40 to 60° C.

8. The method according to claim 1, wherein the cyclization reaction is conducted in the presence of at least one solvent selected from the group consisting of anisole, THF, toluene, xylene and Me-THF.

9. The method according to claim 8, wherein the solvent further comprises Z—OH, where Z is ($C_1$-$C_4$) alkyl, not including t-butyl.

10. The method according to claim 8, wherein the solvent used for the cyclization reaction is an anhydrous solvent.

11. The method according to claim 1, characterized in that further comprising metering in the MO—Z in Z—OH.

12. The method according to claim 1, further comprising adding NaOMethyl to the cyclization reaction.

13. The method according to claim 1, further comprising adding a reagent/solvent to the dealkoxycarbonylation reaction, wherein the reagent/solvent is acetic acid or consists of a mixture of acetic acid and trifluoroacetic acid.

14. The method according to claim 4, wherein:
$R^1$ is ethyl or methyl,
$R^2$ is ethyl or methyl,
M is sodium or potassium, and
Z is ethyl or methyl.

15. The method according to claim 14, wherein:
$R^1$ is methyl,
$R^2$ is methyl,
M is sodium, and
Z is methyl.

16. The method according to claim 5, wherein:
$R^1$ is ethyl or methyl,
$R^2$ is ethyl or methyl,
M is sodium or potassium, and
Z is ethyl or methyl.

17. The method according to claim 16, wherein:
$R^1$ is methyl,
$R^2$ is methyl,
M is sodium, and
Z is methyl.

18. The method according to claim 7, wherein:
$R^1$ is ethyl or methyl,
$R^2$ is ethyl or methyl,
M is sodium or potassium, and
Z is ethyl or methyl.

19. The method according to claim 18, wherein:
$R^1$ is methyl,
$R^2$ is methyl,
M is sodium, and
Z is methyl.

20. The method according to claim 9, wherein:
$R^1$ is methyl,
$R^2$ is methyl,
M is sodium, and
Z is methyl.

* * * * *